United States Patent
Comhair et al.

(10) Patent No.: US 9,410,938 B2
(45) Date of Patent: Aug. 9, 2016

(54) BIOMARKERS FOR ASTHMA

(71) Applicant: The Cleveland Clinic Foundation, Cleveland, OH (US)

(72) Inventors: Suzy Comhair, Concord Township, OH (US); Satish Kalhan, Pepper Pike, OH (US); Stanley Hazen, Pepper Pike, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 13/893,425

(22) Filed: May 14, 2013

(65) Prior Publication Data

US 2013/0315898 A1   Nov. 28, 2013

Related U.S. Application Data

(60) Provisional application No. 61/646,609, filed on May 14, 2012.

(51) Int. Cl.

| | |
|---|---|
| *A61B 5/145* | (2006.01) |
| *A61K 31/40* | (2006.01) |
| *A61K 31/395* | (2006.01) |
| *A61K 47/18* | (2006.01) |
| *G01N 33/483* | (2006.01) |
| *G01N 33/49* | (2006.01) |
| *G01N 33/493* | (2006.01) |

(52) U.S. Cl.
CPC .............. *G01N 33/483* (2013.01); *A61B 5/145* (2013.01); *A61B 5/14546* (2013.01); *A61K 31/395* (2013.01); *A61K 31/40* (2013.01); *A61K 47/183* (2013.01); *G01N 33/49* (2013.01); *G01N 33/493* (2013.01)

(58) Field of Classification Search
None
See application file for complete search history.

(56) References Cited

PUBLICATIONS

Laidlaw et al. 'Plasma and urine taurine levels in vegans.' Am J Clin Nutr 47:660-663, 1988.*
Trautwein et al. 'Taurine concentrations in plasma and whole blood in humans: estimation of error from intra- and interindividual variation and sampling technique.' Am J Clin Nutr 52:758-764, 1990.*
Ghandforoush-Sattari et al. 'Changes in plasma concentration of taurine in stroke.' Neuro. Lett. 496:172-175, 2011.*
Blesa et al. 'Effectiveness of oral N-acetylcysteine in a rat experimental model of asthma.' Pharm. Res. 45(2):135-140, 2002.*
Hofford et al. 'Levels of amino acids and related compounds in bronchoalveolar lavage fluids of asthmatic patients.' Am, J. Respir. Crit. care Med. 155:432-435, 1997.*
Trautwein et al. 'Taurine concentrations in plasma and whole blood in humans:estimation of error from intra- and interindividual variation and sampling technique.' Am. J. Clin. Nutr 52:758-764, 1990.*
Lipworth et al.'Leukotriene-receptor antagonists.' Lancet 353:57-62, 1999.*
Agackiran et al., "The efficiency of proanthocyanidin in an experimental pulmonary fibrosis model: comparison with taurine," Inflammation. Aug. 2012;35(4):1402-10. doi: 10.1007/s10753-012-9453-6.
Cortijo et al., "Effects of taurine on pulmonary responses to antigen in sensitized Brown-Norway rats," Eur J Pharmacol, Nov. 9, 2001; 431(1):111-7.
Deminice et al., "Taurine supplementation does not decrease homocysteine levels and liver injury induced by a choline-deficient diet," Life Sci. Apr. 23, 2014. pii: S0024-3205(14)00426-3. doi: 10.1016/j.lfs.2014.04.015. [Epub ahead of print].
Guler et al., "Taurine attenuates lung ischemia-reperfusion injury after lung transplantation in rats," J Anesth., Nov. 6, 2013. [Epub ahead of print].
Gurujeyalakshmi et al., "Taurine and niacin block lung injury and fibrosis by down-regulating bleomycin-induced activation of transcription nuclear factor-kappaB in mice," J Pharmacol Exp Ther., 2000, 293(1):82-90.
Wenting et al., "Therapeutic effect of taurine against aluminum-induced impairment on learning, memory and brain neurotransmitters in rats," Neurol Sci., 2014, [Epub ahead of print].
Zr et al., "Effects of taurine on the expression of nitric oxide synthase in lung of rats exposed to silica," Zhonghua Lao Dong Wei Sheng Zhi Ye Bing Za Zhi, 2005, 23(2):116-8.

\* cited by examiner

*Primary Examiner* — Nora Rooney
(74) *Attorney, Agent, or Firm* — Casimir Jones, S.C.; Jason R. Bond

(57) ABSTRACT

The present invention provides methods, kits, and compositions related to testing a sample for the level of a biomarker related to asthma, wherein the biomarker is selected from: taurine, maltose, maltotriose, adenosine 5'-monophosphate, phosphoethanolamine, glycerophosphorylcholine, arachidonate, heptanoate, pelargonate, and nicotinamide. In certain embodiments, the level of the biomarker is used to identify therapy effective for treating asthma. In other embodiments, the level of the biomarker is used to identify the presence, severity, or risk of exacerbation of asthma. In further embodiments, the level of the biomarker is used to monitor the response to on-going therapy (e.g., adjust the dosage of the asthma therapy).

3 Claims, 8 Drawing Sheets

BIOMARKERS FOR ASTHMA

The present application claims priority to U.S. Provisional application 61/646,609, filed May 14, 2012, which is herein incorporated by reference in its entirety.

This invention was made with government support under grant numbers T35 HL082544 and P01 HL103453 awarded by the National Institutes of Health. The government has certain rights in the invention.

FIELD OF THE INVENTION

The present invention relates to methods, kits, and compositions related to testing a sample for the level of a biomarker related to asthma, wherein the biomarker is selected from: taurine, maltose, maltotriose, adenosine 5'-monophosphate, phosphoethanolamine, glycerophosphorylcholine, arachidonate, heptanoate, pelargonate, and nicotinamide. In certain embodiments, the level of the biomarker is used to identify therapy effective for treating asthma. In other embodiments, the level of the biomarker is used to identify the presence, severity, or risk of exacerbation of asthma. In further embodiments, the level of the biomarker is used to monitor the response to on-going therapy (e.g., adjust the dosage of the asthma therapy).

BACKGROUND

Approximately 38.4 million Americans have been diagnosed with asthma by a health professional during their lifetime. This chronic inflammatory disease places a significant burden on both the health care system and individual patients, with annual expenditures for health and lost productivity due to asthma estimated at over $20 billion. In spite of high morbidity and costs, most asthmatic patients have mild-to-moderate disease and about 5-8% of asthmatic patients fall into the category of "chronic severe asthma" (CSA). Asthmatic patients have significant reduction in quality of life as a result of their asthma, have frequent hospital admissions and emergency visits, and account for a much larger percentage of overall health care costs. Clinically, asthma is characterized by a component of irreversible airflow obstruction and peripheral airways disease, ongoing mediator release and a reduced association with atopy. There is currently no way to predict whether an individual patient with asthma will be stable over time, or exhibit declining lung function that leads to development of CSA.

Current asthma treatment and diagnosis are predominantly clinically based, or use pulmonary function testing, which is expensive, can only occur in specialized pulmonary function testing laboratories, and is inconvenient. Exhaled breath NO is another recent test used in asthma, but it lacks specificity and sensitivity for diagnosis and monitoring of asthma treatment/severity. Further, it is not readily collected and sent to laboratory for testing, like most other diagnostic tests. Rather, it takes specialized instrumentation to be located on-site for testing. Simple reliable and objective quantitative measures of blood or urine based tests for the diagnosis of asthma, and for predicting risk of exacerbation, need for therapeutic titration, or monitoring of response to therapeutic interventions, are needed.

SUMMARY OF THE INVENTION

The present invention provides methods, kits, and compositions related to testing a sample for the level of a biomarker related to asthma, wherein the biomarker is selected from: taurine, maltose, maltotriose, adenosine 5'-monophosphate, phosphoethanolamine, glycerophosphorylcholine, arachidonate, heptanoate, pelargonate, and nicotinamide. In certain embodiments, the level of the biomarker is used to identify therapy effective for treating asthma. In other embodiments, the level of the biomarker is used to identify the presence, severity, or risk of exacerbation of asthma. In further embodiments, the level of the biomarker is used to monitor the response to on-going therapy (e.g., adjust the dosage of the asthma therapy).

In some embodiments, the present invention provides methods of identifying an efficacious asthma therapy for a subject comprising: a) testing a sample from a subject to determine the level of at least one biomarker selected from the group consisting of: taurine, maltose, maltotriose, adenosine 5'-monophosphate, phosphoethanolamine, glycerophosphorylcholine, arachidonate, heptanoate, pelargonate, and nicotinamide; and b) identifying an asthma therapy that is effective for treating asthma in the subject based on the level of the at least one biomarker that is determined.

In certain embodiments, the at least one biomarker comprises taurine or arachidonate and the asthma therapy comprises a leukotriene receptor antagonist (LTRA) (e.g., montelukast, zafirlukast, Pranlukast and zileuton). In further embodiments, the asthma therapy is administered to the subject. In particular embodiments, the at least one biomarker comprises taurine and the asthma therapy that is administered comprises a leukotriene receptor antagonist (LTRA). In particular embodiments, the asthma therapy comprises a non-steroidal asthma medication. In some embodiments, the asthma therapy comprises a steroidal asthma medication. In certain embodiments, the sample comprises a blood sample, plasma sample, or urine sample (or any other biological sample) from the subject.

In particular embodiments, the present invention provides methods of identifying the presence, severity, or risk of exacerbation of asthma in a subject comprising: a) testing a sample from a subject to determine the level of at least one biomarker selected from the group consisting of: taurine, maltose, maltotriose, adenosine 5'-monophosphate, phosphoethanolamine, glycerophosphorylcholine, arachidonate, heptanoate, pelargonate, and nicotinamide; and b) identifying the presence, severity, or risk of exacerbation of asthma in the subject based on an elevated level of the at least one biomarker.

In certain embodiments, the methods further comprise administering an asthma therapy to the subject. In other embodiments, the methods further comprise informing the subject that they have asthma, the severity of the asthma, and/or the risk of exacerbating the asthma. In particular embodiments, the severity includes: 1) declining lung function, and 2) stable, non-declining lung function.

In some embodiments, the at least one biomarker comprises taurine. In further embodiments, the elevated level of the at least one biomarker is higher than a control level. In particular embodiments, the control level is determined or pre-determined from: i) a sample from the subject when not suffering from symptoms of asthma, ii) a sample from a person, or sample from a plurality of people, without asthma, iii) samples from the general population. In further embodiments, the sample comprises a blood sample, plasma sample, or urine sample from the subject.

In some embodiments, the present invention provides methods of monitoring response to asthma therapy comprising: a) testing a sample from a subject receiving asthma therapy to determine the level of at least one biomarker selected from the group consisting of: taurine, maltose, maltotriose, adenosine 5'-monophosphate, phosphoethanolamine, glycerophosphorylcholine, arachidonate, heptanoate, pelargonate, and nicotinamide; and b) adjusting, or continuing un-adjusted, the asthma therapy based on the level of the at least one biomarker that is determined.

In certain embodiments, the sample comprises a blood sample, plasma sample, or urine sample from the subject. In other embodiments, the at least one biomarker comprises taurine or arachidonate and the asthma therapy comprises a leukotriene receptor antagonist (LTRA) (e.g., montelukast, zafirlukast, Pranlukast and zileuton). In certain embodiments, the present invention provides methods of treating asthma comprising: administering to a subject with asthma an inhibitor of at least one biomarker selected from the group consisting of: taurine, maltose, maltotriose, adenosine 5'-monophosphate, phosphoethanolamine, glycerophosphorylcholine, arachidonate, heptanoate, pelargonate, and nicotinamide. In particular embodiments, the inhibitor comprises an agent selected from the group consisting of: an antibody or fragment thereof, small molecule, antisense, siRNA, or microRNA.

DETAILED DESCRIPTION

Figure 1:
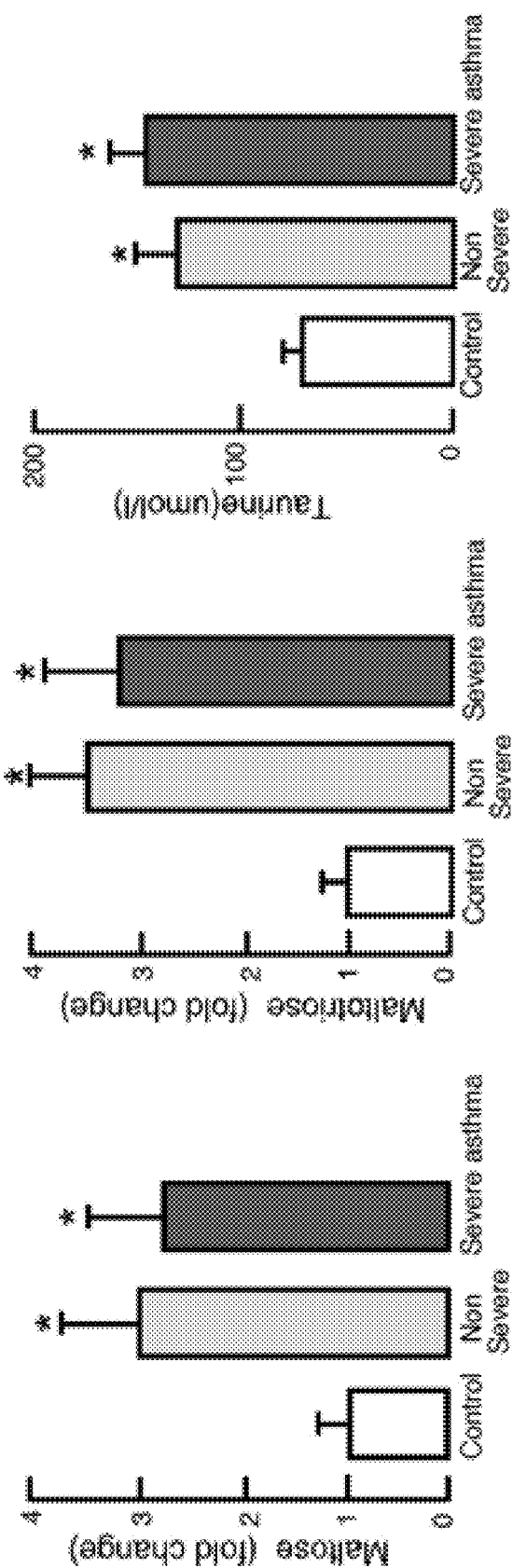
FIG. 1. Maltose, Maltotriose and Taurine in plasma of Control (n=10), non severe (n=10) and severe (n=10) asthmatic individuals. Asthmatic subjects have increased Maltose, Maltotriose and Taurine levels as compared to controls (* T-test, p<0.05).
Figure 2:
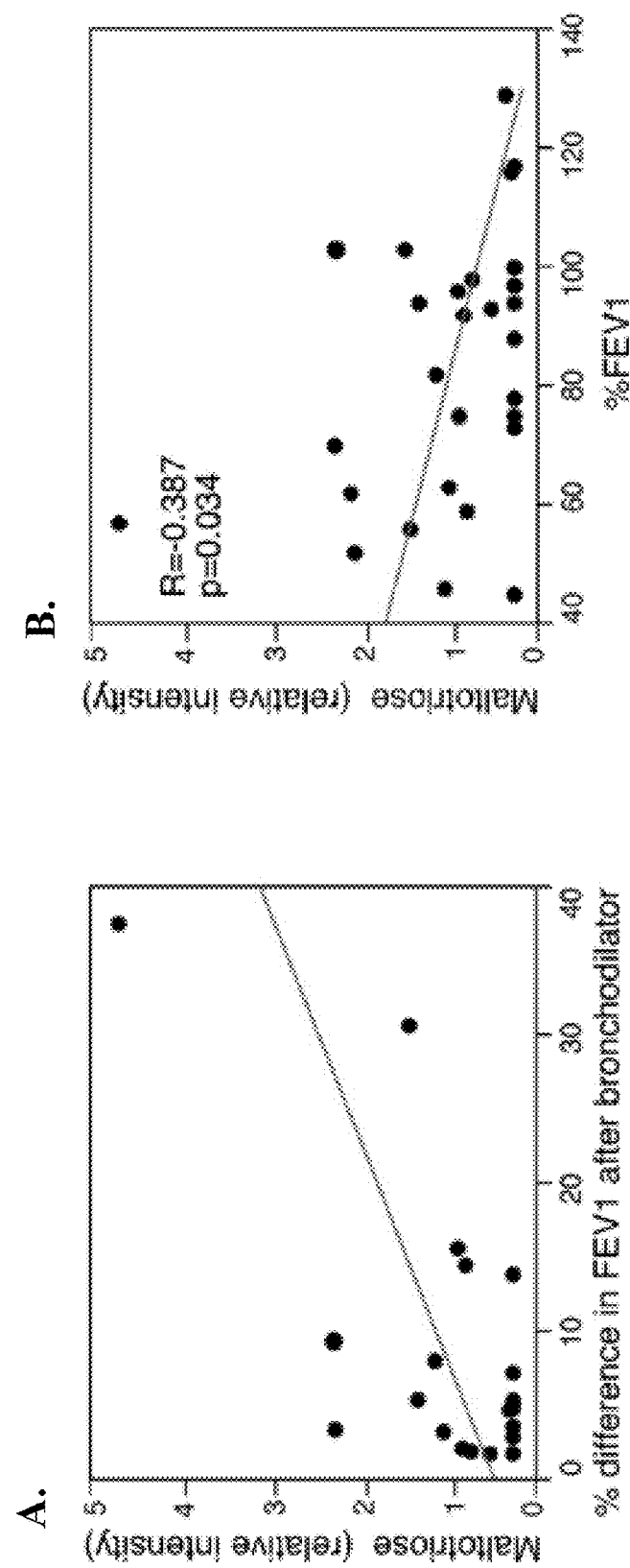
FIGS. 2A and 2B. Correlations of plasma Maltotriose with airflow (% FEV1 and AFEV1). Maltotriose is directly correlated with hyperresponsiveness, as determined by change in FEV1 following Beta-agonist (R=0.602, p=0.002; controls, n=9; non-severe, n=7; and severe, n=8) whereas Maltotriose is inversely correlated with % FEV1 (R=−0.387, p=0.034; controls, n=10; non-severe, n=10; and severe, n=10).
Figure 3:
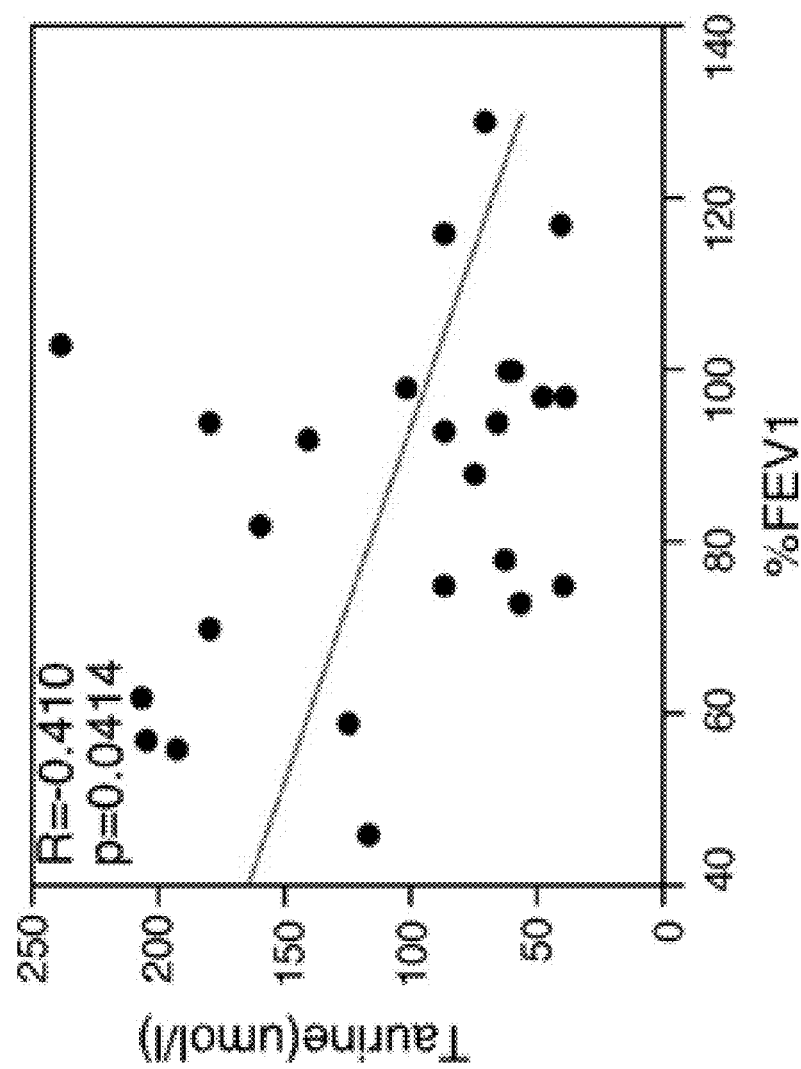
FIG. 3. Correlations of plasma Taurine with airflow as measured by % FEV1. Taurine is inversely correlated with % FEV1 (R=−0.410, p=0.0414; controls, n=10; non-severe, n=9; and severe, n=9).
Figure 4:
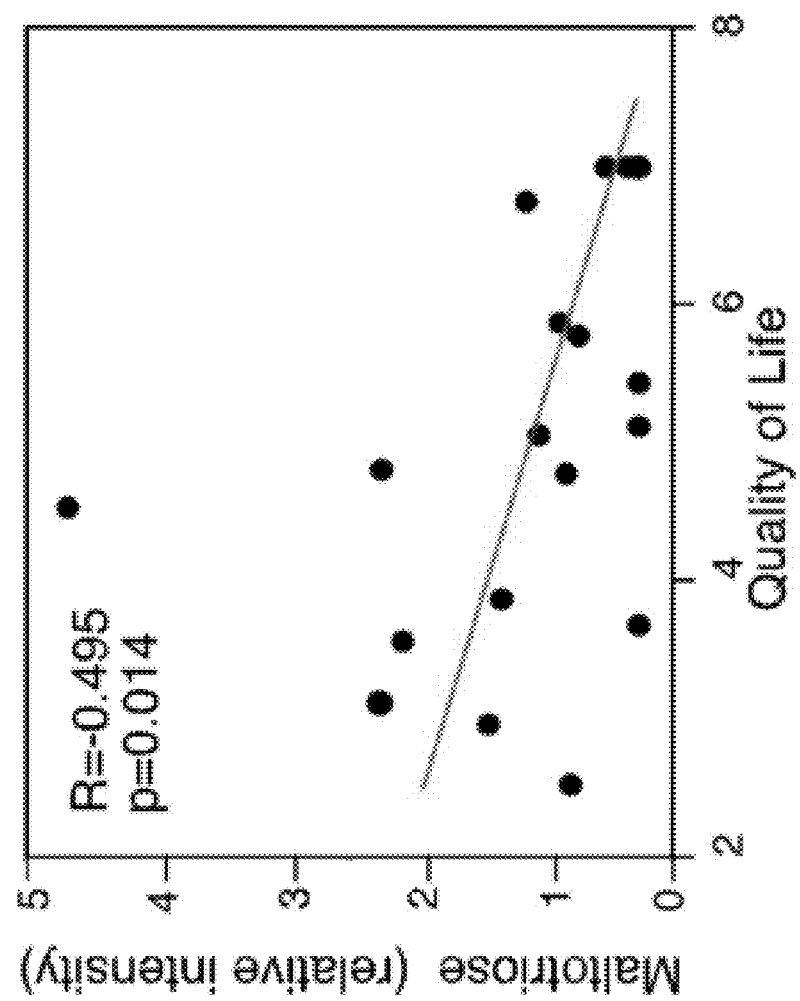
FIG. 4. Correlation of plasma Maltotriose with Quality of life as measured by the Juniper questionnaire. The Juniper questionnaire data suggest subjects with high levels of Maltotriose have a lower total quality of life score than subjects with low levels of Maltotriose. (R=−0.495, p=0.014; controls, n=10; non-severe, n=9; and severe, n=9).
Figure 5:
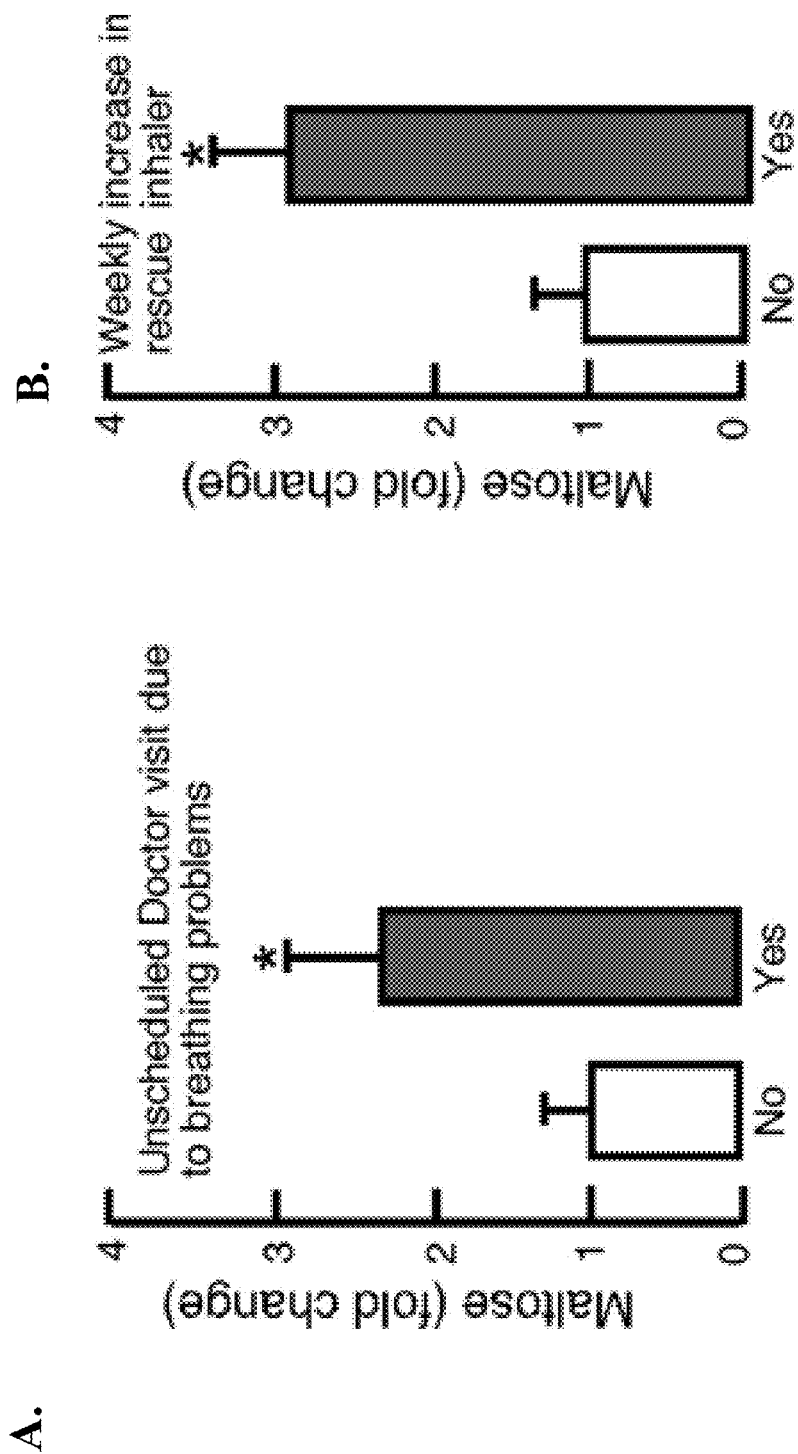
FIGS. 5A and 5B. Health care utilization is related to Maltose levels in plasma. Asthmatic subjects with high levels of Maltose are associated with increased unscheduled doctor visits due to breathing problems (p<0.05) (unscheduled visits: no, n=5, yes, n=14). High levels of Maltose are associated with increased utilization of rescue medication (* T-test, p<0.05) (increased utilization of rescue medication: No, n=8; Yes, n=8).
Figure 6:
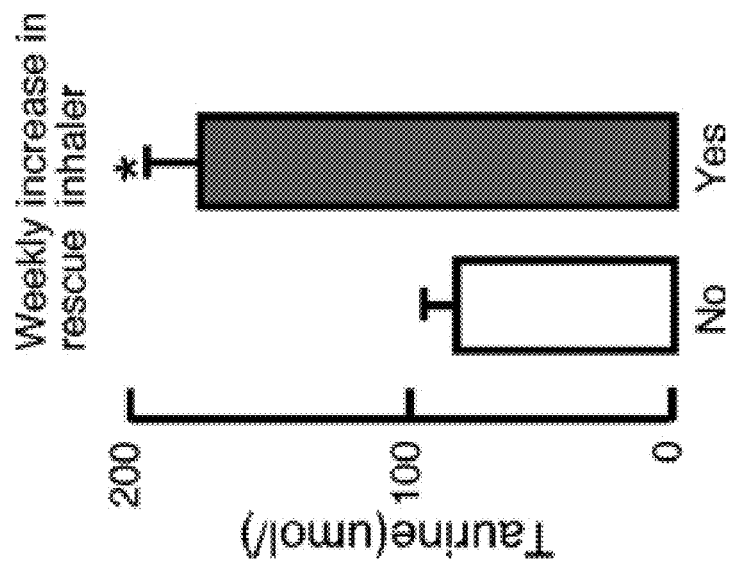
FIG. 6. Health care utilization is related to Taurine levels in plasma. Asthmatic subjects with high levels of Taurine are associated increased utilization of rescue medication (* T-test, p<0.05) (increased utilization of rescue medication: No, n=8; Yes=8).
Figure 7:
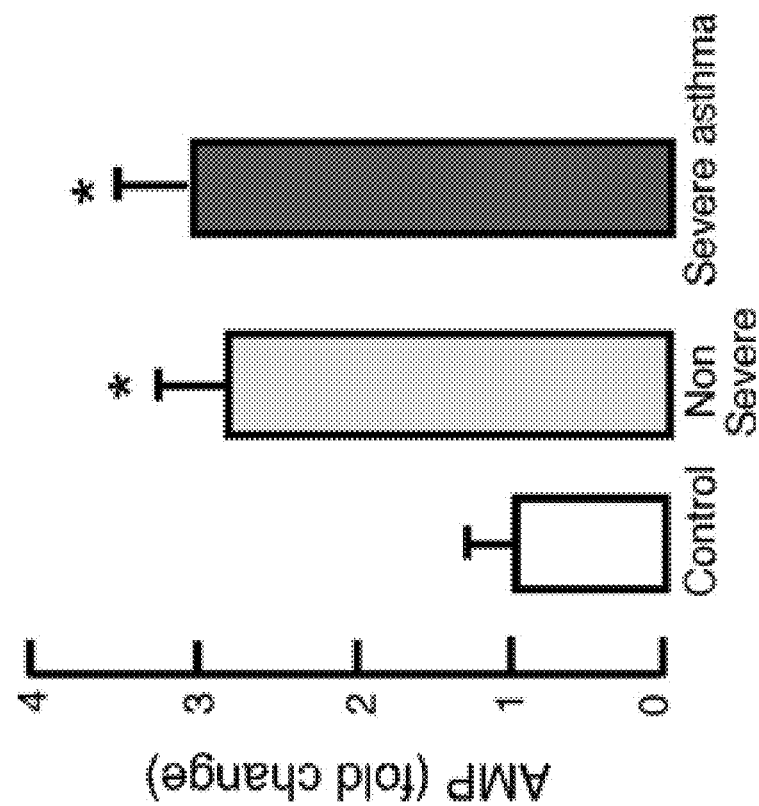
FIG. 7. Increased adenosine 5'-monophosphate (AMP) in plasma of non severe (n=10) and severe (n=10) asthmatic individuals as compared to control (n=10) subjects. Asthmatic subjects have increased adenosine 5'-monophosphate (AMP) levels as compared to controls (* T-test, p<0.05).
Figure 8:
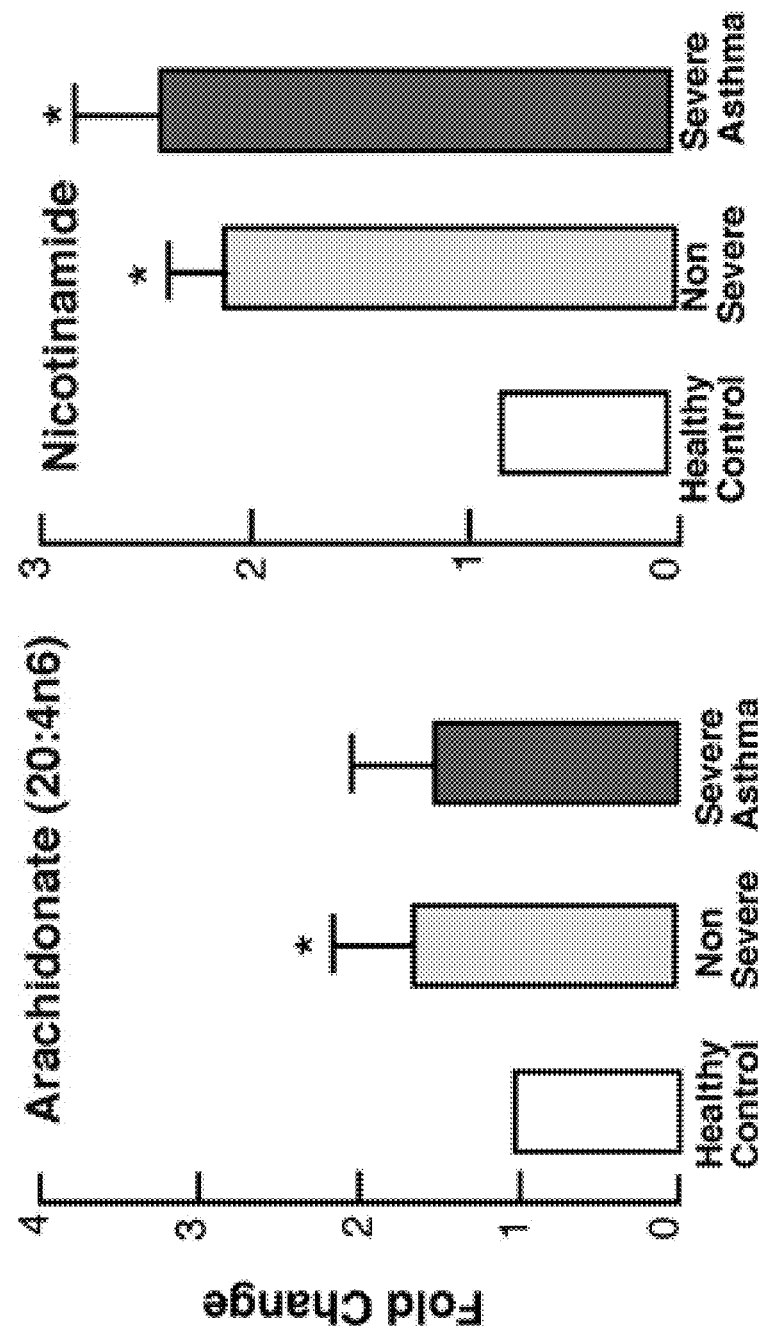
FIG. 8. Increased Arachidonate and Nicotinamide in plasma of non severe (n=10) and severe (n=10) asthmatic individuals as compared to control (n=10) subjects. Arachidonate and Nicotinamide levels as compared to controls (* T-test, p<0.05).

The present invention provides methods, kits, and compositions related to testing a sample for the level of a biomarker related to asthma, wherein the biomarker is selected from: taurine, maltose, maltotriose, adenosine 5'-monophosphate, phosphoethanolamine, glycerophosphorylcholine, arachidonate, heptanoate, pelargonate, and nicotinamide. In certain embodiments, the level of the biomarker is used to identify therapy effective for treating asthma. In other embodiments, the level of the biomarker is used to identify the presence, severity, or risk of exacerbation of asthma. In further embodiments, the level of the biomarker is used to monitor the response to on-going therapy (e.g., adjust the dosage of the asthma therapy).

The present invention is noted limited to any particular method to measure the biomarkers of the present invention. In certain embodiments, the biomarkers are measured within plasma, serum or blood, or non-invasively through urine.

Work conducted during the development of the present invention identified increased levels of biomarkers, such as taurine, maltose, maltotriose, and AMP, as associated with asthma. While the present invention is noted limited to any particular mechanism, and an understanding of the mechanism is not necessary to practice the invention, it may be that the significant increase in taurine levels in asthmatic subjects may be mechanistically linked to asthma via up-regulation of the leukotriene pathway. It is thus remarkable that leukotriene receptor antagonists (LTRAs) are currently used in clinical practice to treat asthma but are only effective in approximately 20% of asthmatic patients and, until the present invention there was no way to predict who will respond to LTRAs. Use of systemic levels of taurine to help identify those who will benefit from LTRAs, or to monitor therapeutic effect and dose adjustments, is a beneficial application of taurine levels in the treatment monitoring of asthma. Taurine may thus be used for a more tailored, individualized approach to asthma management. Asthma medications in general have wide variations in efficacy and additional information about who will respond to LTRAs vs alternative agents can have important clinical implications and assist in clinical decision making.

Word conducted during development of embodiments of the present invention also found that plasma, serum and blood based levels of adenosine 5'-monophosphate (AMP), maltose and maltotriose are higher is asthmatics subjects as compared to controls, which suggest derangements in the cellular energetic pathways and a possible response to altered membrane integrity in response to inflammation. As such, these markers may also serve as diagnostic and prognostic indicators of asthma presence, risk for exacerbation, and as targets for monitoring asthma related therapies.

The quantification of the biomarkers of the present invention can be achieved using any suitable methodology, including but not limited to mass spectrometry, HPLC/UV or HPLC/Vis, and other analytical approaches.

In certain embodiments, as part of the methods of the present invention, a patient is administered or recommended for administration steroidal therapeutic agents for treating asthma or other condition. Table 1 below list exemplary steroidal therapeutic agents. In other embodiments, a patient is administered or recommended for administration non-steroidal therapeutic agents. Table 2 provides exemplary therapeutic agents.

TABLE 1

Steroidal Drugs

| Generic Name | Chemical Name | Brand Name |
|---|---|---|
| Beclomethasone Dipropionate HFA | 9-chloro-11β,17,21-trihydroxy-16βmethylpregna-1,4-diene-3,20-dione 17,21-dipropionate. | QVAR Inhalation Aerosol 40 mcg/puff & 80 mcg/puff |
| Budesonide | 16,17-(butylidenebis(oxy))-11,21-dihydroxy-, (11-β,16-α)-pregna-1,4-diene-3,20-dione | Plumicort Flexhaler & Plumicort Respules |
| Budesonide in combination with Formoterol | (RS)-11β,16α,17,21-Tetrahydroxypregna-1,4-diene-3,20-dione cyclic 16,17-acetal with butyraldehyde (Budesonide) (R*,R*)-(±)-N-[2-hydroxy-5-[1-hydroxy-2-[[2-(4-methoxyphenyl)-1-methylethyl]amino]ethyl]phenyl]formamide, (E)-2-butenedioate(2:1), dihydrate | Symbicort |
| Ciclesonide | 2-[(1S,2S,4R,8S,9S,11S,12S,13R)-6-cyclohexyl-11-hydroxy-9,13-dimethyl-16-oxo-5,7-dioxapentacyclo [10.8.0.02,9.04,8.013,18] icosa-14,17-dien-8-yl]-2-oxoethyl 2-methylpropanoate | Alvesco Inhalation Aerosol |
| Flunisolide | (1S,2S,4R,8S,9S,11S,12S,13R,19S)-19-fluoro-11-hydroxy-8-(2-hydroxyacetyl)-6,6,9,13-tetramethyl-5,7-dioxapentacyclo[10.8.0.02,9.04,8.013,18]icosa-14,17-dien-16-one | Aerobid Aerosol and Aerobid-M Aerosol |
| Fluticasone Propionate | S-(fluoromethyl)-6α,9-difluoro-11β,17-dihydroxy-16α-methyl-3-oxoandrosta-1,4-diene-17β-carbothioate, 17-propanoate | Flovent HFA and Flovent Diskus |
| Fluticasone in combination with Salmeterol (broncodialator) | S-(fluoromethyl)-6α,9-difluoro-11β,17-dihydroxy-16α-methyl-3-oxoandrosta-1,4-diene-17β-carbothioate, 17-propanoate [and] (RS)-2-(hydroxymethyl)-4-{1-hydroxy-2-[6-(4-phenylbutoxy)hexylamino]ethyl}phenol | Advair Diskus & Advair HFA |
| Mometasone furoate | (11β,16α)-9,21-dichloro-11-hydroxy-16-methyl-3,20-dioxopregna-1,4-dien-17-yl 2-furoate | Asmanex Twisthaler |
| Mometasone in combination with Formoterol (broncodialtor) | (11β,16α)-9,21-dichloro-11-hydroxy-16-methyl-3,20-dioxopregna-1,4-dien-17-yl 2-furoate [and] rac-(R,R)-N-[2-hydroxy-5-[1-hydroxy-2-[1-(4-methoxyphenyl)propan-2-ylamino]ethyl] phenyl]formamide | Dulera |
| Triamcinolone acetonide | (4aS,4bR,5S,6aS,6bS,9aR,10aS,10bS)-4b-fluoro-6b-glycoloyl-5-hydroxy-4a,6a,8,8-tetramethyl-4a,4b,5,6,6a,6b,9a,10,10a,10b,11,12-dodecahydro-2H-naphtho[2',1':4,5]indeno[1,2-d][1,3]dioxol-2-one | Azmacort Inhalation Aerosol |
| Prednisone | 17,21-dihydroxypregna-1,4-diene-3,11,20-trione | Deltasone |
| Prednisolone | (11β)-11,17,21-trihydroxypregna-1,4-diene-3,20-dione | |
| Methylprednisolone | (1S,2R,8S,10S,11S,14R,15S,17S)-14,17-dihydroxy-14-(2-hydroxyacetyl)-2,8,15-trimethyltetracyclo[8.7.0.02,7.011,15]heptadeca-3,6-dien-5-one | Medrol, Solu-Medrol, Depo-Medrol |
| Dexamethasone | (8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one | Decadron |

TABLE 2

Non-Steroidal Drugs

| Generic Name | Chemical Name | Brand Name | Type |
|---|---|---|---|
| Albuterol Sulfate | α1 [(tert-butylamino) methyl]-4-hydroxy-m-xylene-α,α'-diol sulfate (2:1) (salt) | VoSpireER Extended Release Tablets | LABA - recommended with use with steroids |
| Formoterol fumarate | ±)-2-hydroxy-5-[(1RS)-1-hydroxy-2-[[(1RS)-2-(4-methoxyphenyl)-1methylethyl]-amino]ethyl]formanilide fumarate dihydrate | Foradil Aerolizer | LABA - recommended with use with steroids |
| Salmeterol Xinafoate | ±-4-Hydroxy-α1-[[[6-(4-phenylbutoxy)hexyl]amino]methyl]-1,3-benzenedimethanol compd. with 1-hydroxy-2-naphthalenecarboxylic acid (1:1) | Serevent Diskus | LABA - recommended with use with steroids |

TABLE 2-continued

Non-Steroidal Drugs

| Generic Name | Chemical Name | Brand Name | Type |
|---|---|---|---|
| Albuterol Sulfate HFA | α1-[(tertbutylamino) methyl]-4-hydroxy-m-xylene-α,α'-diol sulfate (2:1) (salt) | ProAir HFA, Proventil HFA, Ventolin HFA | SABA - rescue medicine |
| Albuterol Sulfate Inhalation Solution | α1 [(tert-butylamino) methyl]-4-hydroxy-m-xylene-α,α'-diol sulfate (2:1) (salt) | | SABA - rescue medicine |
| Albuterol Sulfate Nebulizer Soluction | α1 [(tert-butylamino) methyl]-4-hydroxy-mxylene-α,α'-diol sulfate (2:1) (salt) | AccuNeb Inhalation Solution, Albuterol Sulfate 0.5% | SABA - rescue medicine |
| Ipratropium Bromide in combination with Albuterol Sulfate | [8-methyl-8-(1-methylethyl)-8-azoniabicyclo[3.2.1] oct-3-yl] 3-hydroxy-2-phenyl-propanoate [and] α1 [(tert-butylamino) methyl]-4-hydroxy-mxylene-α,α'-diol sulfate (2:1) (salt) | Combivent; DuoNeb | Anticholinergic |
| Ipratropium Bromide HFA | [8-methyl-8-(1-methylethyl)-8-azoniabicyclo[3.2.1] oct-3-yl] 3-hydroxy-2-phenyl-propanoate | Atrovent, Apovent and Aerovent | Anticholinergic |
| Levalbuterol HCl | (R)-α1-[[(1,1-dimethylethyl)amino]methyl]-4-hydroxy-1,3-benzenedimethanol hydrochloride | Xopenex; Xopenex HFA | SABA - rescue medicine |
| Pirbuterol | (RS)-6-[2-(tert-butylamino)-1-hydroxyethyl]-2-(hydroxymethyl)pyridin-3-ol | Maxair Autoinhaler | SABA - rescue medicine |
| Tiotropium Bromide Inhalation Powder | (1α,2β,4β,5α,7β)-7-[(Hydroxydi-2-thienylacetyl)oxy]-9,9-dimethyl-3-oxa-9-azoniatricyclo[3.3.1.02,4]nonane bromide monohydrate | Spiriva HandiHaler | SABA - rescue medicine |
| Terbutaline | (RS)-5-[2-(tert-butylamino)-1-hydroxyethyl]benzene-1,3-diol | Brethine, Bricanyl, Brethaire, Terbulin | SABA - rescue medicine |
| Cromolyn Sodium | disodium 5,5'-[(2-hydroxytrimethylene)dioxy]bis[4-oxo-4H-1-benzopyran-2-carboxylate] | Intal, Intal Metered Dose Inhaler | Non-steroid anti-inflammatory |
| Theophylline | 1H-Purine-2,6-dione,3,7-dihydro,1,3-dimethyl- | Uniphyl, Elixophyllin, Theo-24, Theo-Time, Theochron | Non-steroid anti-inflammatory |
| Montelukast | (S,E)-2-(1-((1-(3-(2-(7-chloroquinolin-2-yl)vinyl)phenyl)-3-(2-(2-hydroxypropan-2-yl)phenyl)propylthio)methyl)cyclopropyl)acetic acid | Singular, Montelo-10 | Leukotriene receptor antagonist (LTRA) |
| Zafirlukast | cyclopentyl 3-{2-methoxy-4-[(o-tolylsulfonyl)carbamoyl]benzyl}-1-methyl-1H-indol-5-ylcarbamate | Accolate, Accoleit, Vanticon | Leukotriene receptor antagonist (LTRA) |
| Zileuton | N-[1-(1-benzothien-2-yl)ethyl]-N-hydroxyurea | Zyflo, Zyflo CR | Leukotriene receptor antagonist (LTRA) |
| Omalizumab | Accession Number DB00043 | Xolair | Humanized Antibody |
| Dyphylline | 7-(2,3-dihydroxypropyl)-theophylline | Lufyllin | Broncodilator |
| Dyphylline in combination with Guaifenesin | 7-(2,3-dihydroxypropyl)-theophylline [and] (RS)-3-(2-methoxyphenoxy)propane-1,2-diol | Lufyllin-COPD; Lufyllin-GG | Broncodilator and expectorant |

EXAMPLES

Example 1

Asthma Biomarker Identification

This Examples describes methods used to identify biomarkers of asthma in patient samples.
Methods
The plasma profiles of 10 asthmatic subjects and 10 healthy controls were examined using an untargeted global metabolomic analysis. The metabolic profiling platform was composed of ultrahigh performance liquid chromatography/tandem mass spectrometry (UHKC/MS/MS) and gas chromatography (GC/MS). Amino acid concentrations were determined by high-performance liquid chromatography. Statistical analysis was performed using JMP v.9.0.0 (SAS Inc. Cary, N.C.).

Taurine, adenosine 5'-monophosphate (AMP), maltose and maltitriose concentrations were determined by ultrahigh performance liquid chromatography/tandem mass spectrometry (UHPLC/MS/MS) and gas chromatography (GC/MS). UPLC/MS was carried out using a Waters Acquity UHPLC (Waters Corporation, Milford, Mass.) coupled to an LTQ mass spectrometer (Thermo Fisher Scientific Inc., Waltham, Mass.) equipped with an electrospray ionization source. Two separate UHPLC/MS injections were performed on each sample: one optimized for positive ions and one for negative ions. Derivatized samples for GC/MS were analyzed on a Thermo-Finnigan Trace DSQ fast-scanning single-quadrupole MS operated unit mass resolving power. Chromatographic separation followed by full scan mass spectra was carried to record retention time, molecular time (m/z) and MS/MS of all detectable ions presented in the samples.

A log transformation was applied to the observed relative concentrations for each biochemical to account for variance increasing as a function of a biochemical's average response. Student's t-tests were used to compare groups with equal variance; Welch's t-tests were used to compare groups with unequal variance.

Results

Of the 293 metabolites, 15 metabolites were significantly increased in asthma as compared to healthy control subjects (all $p<0.05$). General categories of the metabolites included the carbohydrate and lipid metabolic pathways. Linear glycogen polymers maltose and maltotriose were increased 3- and 4-fold, respectively, in asthma as compared to controls (see Figures). Asthmatics had increased lipid metabolites, including 2-fold increase in glycerolipid metabolites phosphoethanolamine and glycerophosphorylcholine, 1.4-fold increase in the long-chain fatty acid arachidonate as well as 1.4-fold increase in the medium-chain fatty acids heptanoate and pelargonate (see Figures). Purine analyses showed 2.7-fold increase in adenosine 5'-monophosphate (AMP) (see Figures). The cofactor nicotinamide (NAD+) was 2.2-fold higher in asthma (see Figures). Amino acids were similar between groups, except taurine, which was 2-fold higher in asthma (see Figures).

Lipid Metabolites in Plasma of Controls (N=10) and all Asthmatic Subjects (Non-Severe and Severe Asthma)

| Scaled imputed Intensity | Control (N = 10) | Asthma (N = 20) | |
|---|---|---|---|
| phosphoethanolamine | 0.47 (0.1) | 0.86 (0.1) | P = 0.03 |
| glycerophosphorylcholine | 0.81 (0.10 | 1.34 (0.1) | P = 0 006 |
| heptanoate | 0.81 (0.10 | 1.21 (0.08) | P = 0.04 |
| pelargonate | 0.91 (0.1) | 1.21 (0.1) | P = 0.06 |

Data are represented as mean (SE). The lipid metabolites are presented as scaled imputed Intensity.

CONCLUSIONS

Asthmatic individuals have unique plasma metabolite levels that distinguish them from healthy controls and indicate activation of specific inflammatory pathways. For example, high levels of arachidonate and taurine are consistent with greater activation of the leukotriene pathway in asthma. Phospholipase-A2 generates arachidonic acid which controls a selective, volume-sensitive osmolyte transporter that modulates intracellular taurine efflux into plasma. Thus, plasma taurine can serve as a biomarker for activation of the leukotriene pathway. Also, while the present invention is not limited to any particular mechanism, and an understanding of the mechanism is not necessary to practice the present invention, the general increase in glycerolipid substrate may enable the greater arachidonic acid production. In contrast, elevated maltose, maltotriose, AMP and NAD+ suggest derangements in the cellular energetic pathways. Inefficient cellular energetics might explain the increase in plasma levels of linear glycogen polymers.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of testing and treating a subject with asthma comprising:
   a) testing a plasma sample from a subject with asthma to determine the level of taurine, wherein said testing is performed by the use of liquid chromatography, gas chromatography, and/or mass spectrometry; and
   b) administering asthma therapy to said subject based on said level of taurine,
   wherein said asthma therapy is a non-steroidal therapeutic agent that is a leukotriene receptor antagonist (LTRA) if said level of taurine is at least 2-fold increased compared to a control level, and
   wherein said asthma therapy is a steroidal therapeutic agent if said level of taurine is not at least 2-fold increased compared to a control level.

2. The method of claim 1, wherein said LTRA comprises montelukast.

3. The method of claim 1, wherein said LTRA comprises zafirlukast.

* * * * *